United States Patent [19]

Vistica

[11] Patent Number: 4,772,632
[45] Date of Patent: Sep. 20, 1988

[54] ANTINEOPLASTIC, SYSTEM - L SPECIFIC AMINO ACID NITROGEN MUSTARDS

[75] Inventor: David T. Vistica, Damascus, Md.

[73] Assignee: The United States of America as represented by the Department of Health and Human Services, Washington, D.C.

[21] Appl. No.: 17,701

[22] Filed: Feb. 24, 1987

[51] Int. Cl.$^4$ .......................................... A61K 31/195
[52] U.S. Cl. ..................................... 514/561; 562/456
[58] Field of Search ................. 502/456, 457; 514/501

[56] References Cited

U.S. PATENT DOCUMENTS 3,532,744 10/1970 Fletcher et al. ..................... 562/457
3,704,312 11/1972 Russell et al. ....................... 562/457

OTHER PUBLICATIONS

Conners et al., J. Chem. Soc., pp. 2994–3007 (1960).
Kilberg *Federation Proceedings* 45:2483–2454, "Amino Acid Transport in Eukaryotic Cells and Tissues", 1986.
Mauger et al., *Biochemical Pharmacology* 11:847–858, "ARL-2-Halogenoalkylamines-XX", 1962.

*Primary Examiner*—James H. Reamer
*Attorney, Agent, or Firm*—Holman & Stern

[57] ABSTRACT

New antineoplastic, system - L specific amino acid nitrogen mustards with reduced myelosuppressive effect are disclosed. A method for identifying and isolating the cellular component comprising the L - amino acid transport system is also described.

2 Claims, 5 Drawing Sheets

ANTINEOPLASTIC, SYSTEM - L SPECIFIC AMINO ACID NITROGEN MUSTARDS

BACKGROUND OF THE INVENTION

Technical Field

The present invention is related generally to phenylalanine mustards. More particularly, the present invention is related to the synthesis of new, system L specific amino acid nitrogen mustards useful as antineoplastic agents and as probes for identifying the L-amino acid transport system.

State of the Art

The phenyalanine mustards, a group of antitumor agents of the alkylating agent class, were synthesized in the 1950's and found to possess a broad range of antitumor activity aginst both experimental and human neoplasms. These antitumor agents incorporated into their structure the physiological amino acid carrier phenylalanine and the cytotoxic bis(2-chloroethyl) amino group. However, even though effective as antitumor agents, the degree of myelosuppression produced by this group of antineoplastic compounds was found to be undesirable and dose-limiting. Hence, the need to develop more selective antitumor agents inter alia with reduced myelosuppressive activity became obvious.

SUMMARY OF THE INVENTION

It is, therefore, an object of the present invention to provide improved antineoplastic agents, transported by system L which exhibit reduced myelosuppressive activity compared to the prototype L-phenylalanine mustard (L-PAM).

It is a further object of the present invention to provide a specific probe for identifying the L-amino acid transport system.

It is an additional object of the present invention to provide a method for treating neoplasms by administering to a susceptible or inflicted host the nitrogen mustards of the present invention in an amount effective to inhibit growth of the neoplasm.

Various other objects and advantages will become evident as the detailed description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 shows proton decoupled $^{13}$C-nmr Spectra of compound 3.

(a) Fully coupled spectrum. (b) H-1 and H-4 decoupled spectrum. (c) H-1, H-3, and H-4 decoupled spectrum. The doublet of doublets ($^1$J residual=147 Hz and $^3$J residual=7 Hz) centerd at 134.1 ppm is due to c-8;

FIG. 2 shows selectively proton decoupled $^{13}$C-NMR Spectra of compound 2.

(a) Fully coupled spectrum. (b) H-1 and H-4 decoupled spectrum. (c) H-1, H-3 and H-4 decoupled spectrum. The small peaks downfield of the doublet of triplets and 145.8 ppm are due to slight impurities in the sample;

FIG. 3 shows competitive inhibition of the initial velocity of transport of 2-aminobicyclo [2.2.1]heptane-2-carboxylic acid by L-PAM and compound 6.

Panel A: Compound 6. $K_i$=0.22 $\mu$M±0.02 [mean±S.E. (n=3)].

Panel B: L-PAM. $K_i$=111.6 $\mu$M±7.7 [mean±S.E. (n=4)].

Initial velocity (v) is expressed as picomoles/10$^{-6}$cells/minute.

Antitumor and myelosuppressive activity was determined as described in the text. The therapeutic index was calculated by the following equation;

$$\text{L-PAM: } LD_{90} \frac{\text{CFU-C}}{\text{L1210}} = \frac{14 \, \mu M}{35 \, \mu M} = 0.40.$$

$$\text{Compound 6: } LD_{90} \frac{\text{CFU-C}}{\text{L1210}} = \frac{23.8 \, \mu M}{26.5 \, \mu M} = 0.9.$$

DETAILED DESCRIPTION OF THE INVENTION

The above and various other objects and advantages of the present invention are achieved by providing DL-2-amino-7-bis(2-chloroethyl)amino-1,2,3,4-tetrahydro-2-naphthoic acid or derivatives thereof.

Unless defined otherwise, all technical and scientific terms used herein have the same meaning as commonly understood by one of ordinary skill in the art to which this invention belongs. Although, any methods and materials similar or equivalent to those described herein can be used in the practice or testing of the present invention, the preferred methods and materials are now described. All publications mentioned hereunder are incorporated herein by reference.

All chemical reagents utilized for synthesis were purchased from Aldrich Chemical Co., Milwaukee, Wis. Following the standard procedures, melting points were determined on a Thomas-Hoover apparatus and are uncorrected; proton NMR spectra were determined on Carian T-60 and XL-200 instruments. Chemical shifts are given as δ values with reference to Me$_4$Si. Elemental analyses were commercially obtained from Galbraith Laboratories, Knoxville, Tenn. Coupled with and selectively decoupled $^{13}$C-NMR studies were conducted on Carian XL-200 instrument on saturated Me$_2$SO-d$_6$ samples. Chemical shifts were determined by reference to the Me$_2$SO-d$_6$ peak at 39.5 ppm relative to Me$_4$Si. The spectra were accumulated with a total time of 3.5 sec between transmitter pulses and 30,016 data points. The fully coupled spectra were enhanced by irradiation of the aliphatic proton region during the delay period. Spectra were processed using a resolution enhancement parameter which was manually adjusted for an optimum resolution to noise ratio.

Microscale trimethylsilylation of compounds 6 and 7 was conducted at room temperature (about 22° C. to 27° C.) with a large excess of a 1:2 (v/v) solution of bis(-trimethysilyl)trifluoroacetamide (BSTFA) and redistilled acetonitrile. Gas chromatography (GC) of these derivatives was accomplished with a Varian 2740 GC equipped with a flame ionization detector and interfaced to a Spectra-Physics 4100 computing integrator. A 1.83 mx 2 mm i.d. glass column packed with 3%

OV-17 on 100/120 mesh Gas-Chrom Q was operated with a temperature program from 220° F. to 280° F. at a 4°/min after being held at the inital temperature for 2 min. Typical GC operating conditions employed as injector and detector temperature of 250° F., a 30 mL/min flow rate for both helium carrier gas and hydrogen, and a 300 mL/min flow rate for air.

Electron impact mass spectra were obtained on a DuPont instrument 21-492B interfaced to a VG 2035 data system. Samples were introduced via a Varian 2740 GC (492) in a standard manner and interfaced to the mass spectrometer by a single-stage glass jet separator. Typical operating conditions were: jet separator, 210°; transfer line, 230°; ion source, 245°; acceleration voltage, 1.6 kV; resolution, 1000; electron energy, 75 eV; ionizing current 250 µA; scan speed, 2 s/decade.

DL-2-aminobicyclo[2.2.1]heptane-2-carboxylic acid [carboxyl-$^{14}$C] (4.78 mCi/mmol) was obtained from New England Nuclear, Boston, MA. RPMI (Roswell Park Memorial Institute) 1630 medium, McCoy's 5A medium and Dulbecco's phosphate buffered saline were obtained from GIBCO Laboratories, Chagrin Falls, OH. Salt-free bovine serum albumin was obtained from Advanced Biotechnologies Inc., Silver Spring, MD. Versilube F-50 silicone oil was obtained from the General Electric Co., Waterford, NY. Unless noted otherwise, all procedures or tests mentioned herein were performed following standard methodology well known to one of ordinary skill in the art to which this invention belongs.

SYNTHESIS OF SPECIFIC COMPOUNDS

Figure 1A:
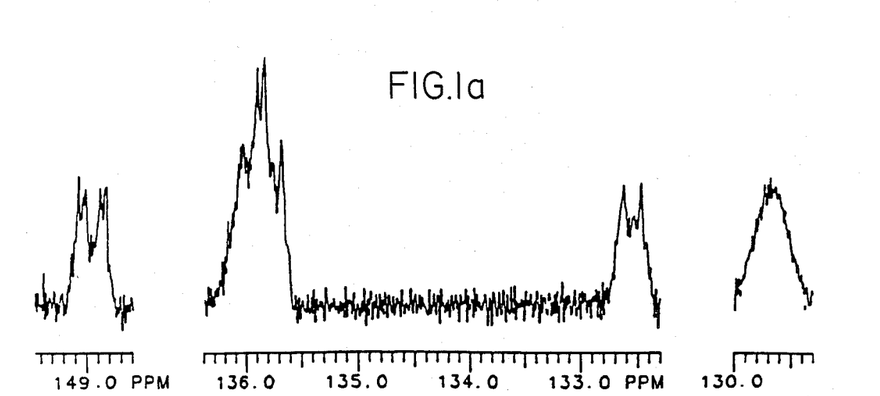
Figure 1B:
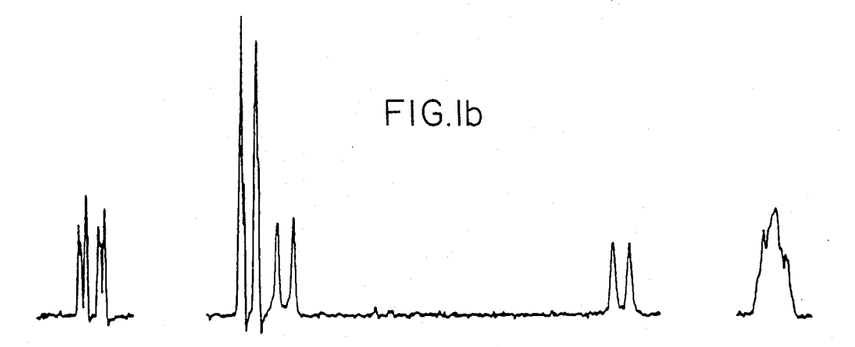
Figure 1C:
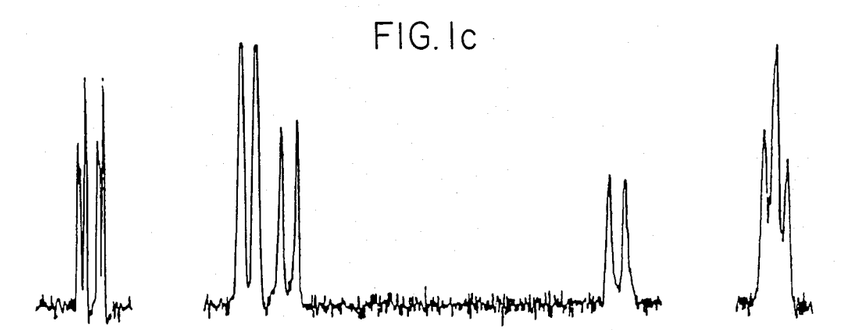
Figure 2A:
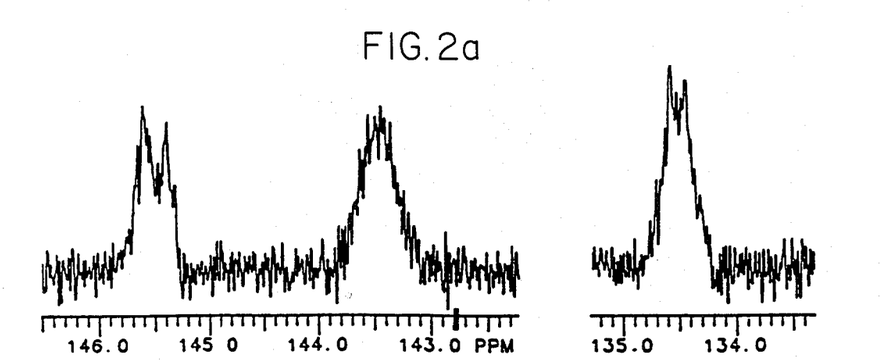
Figure 2B:
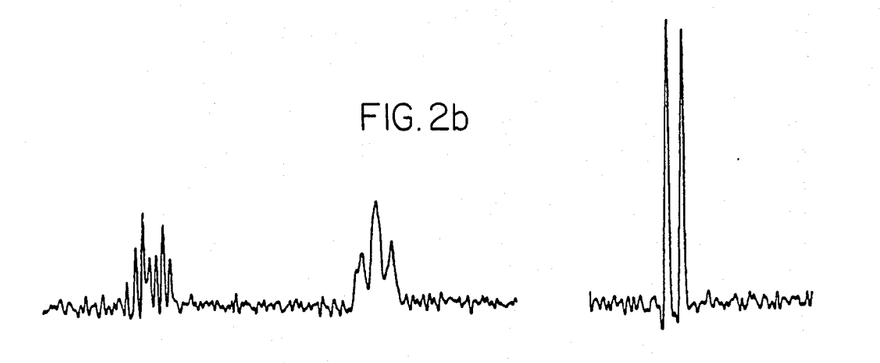
Figure 2C:
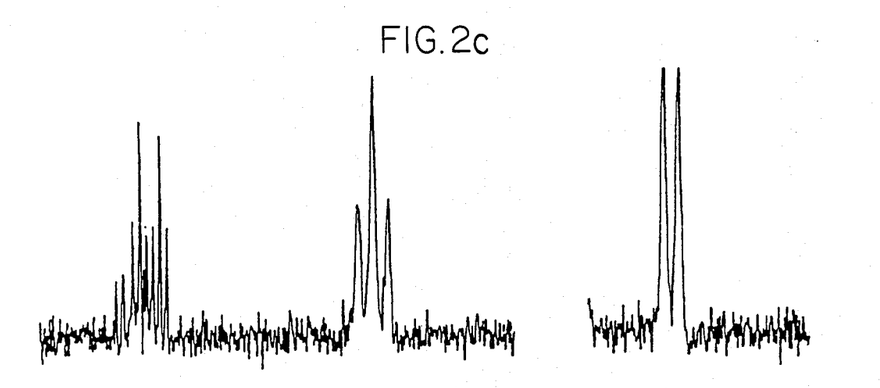

DL-7'-Nitrospiro[2,5-imidazolidinedione-4,2'(1'H-3',4'-dihydronaphthalene](2) and DL-5'-nitrospiro[2,5-imidazolidinedione-4,2'(1'H)-3',4'-dihydrohaphthalene](3)

β-Tetralone hydantoin (20.0 g, 0.092 mol) was added during 4 h to stirred concentrated nitric acid (200 ml, d=1.42) at room temperature (about 22° C.-27° C.). The reaction mixture was then stirred for an additional hour, and water (300 ml) was added slowly. A mixture of two mono-nitro compounds separated out as a granular solid (19.6 g, 81%), mp 240° C., as described by Mauger and Ross, *Biochem Pharmacol.*, 1962, 11: 847. A small sample (0.4 g) of this mixture was separated on a Waters LC-500 preparative HPLC apparatus using two silica gel columns and eluting with ethyl acetate/hexane (1:1). The 7'-nitro isomer (mp 300° C.) as well as the 5'-nitro isomer (mp 260° dec.) were characterized by $^1$H- and $^{13}$C-NMR studies (FIGS. 1 and 2).

Compound 2 (slower moving isomer; $^1$H-NMR (Me$_2$SO-d$_6$) δ 1.95 (m, 2H, CH$_2$-3'), 3.10 (M, 4H, CH$_2$-4'), 7.35 (D, 1H, J=8.2 Hz, H5'), 7.92 (m, 2H, H6' and H8'), 8.35 (s, 1H, N$_3$—H), 10.70 (s, 1H, N$_1$-H); $^{13}$C-NMR (Me$_2$SO-d$_6$) 25.2 (C-4'), 29.6 (C-3'), 36.7 (C-1'), 60.1 (C-2'), 120.7 (C-6'), 123.7 (C-8'), 129.7 (C-5'), 134.6 (C-8'a), 143.5 (C-4'a), 145.5 C-7'), 156.2 (C-4), 177.7 (C-2).

Compound 3 (faster moving isomer); $^1$H-NMR 1.95 (m, 2H, CH$_2$-3'), 3.10 (m, 4H, CH$_2$-1' and CH$_2$-4'), 7.40 (m, 2H, H-7' and H-8'), 7.78 (dd, 1H, J=7.8 Hz, J'=1.6 Hz, H-6'), 8.30 (s, 1H, N$_3$-H), 10.75 (s, 1H, N$_1$-H); $^{13}$C-NMR (Me$_2$So-d$_6$) δ 21.9 (C-4'), 29.3 (C-3'), 37.0 (C-1'), 59.7 (c-2'), 122.2 (C-6'), 126.5 (C-7'), 129.6 (C-4'a), 134.1 (C-8'), 136.0 (C-8'a), 148.9 (C-5'), 156.2 (C-4), 177.7 (C-2).

DL-5'-[Bis(2-hydroxyethyl)amino]sprio[2,5-imidazolidinedione-4,2'(1'H)-3',4'-dihydronaphthalene](5a) and DL-7'-[bis(2-hydroxyethyl-amino]sprio[2,5-imidazolidinedione-4,2'(1'H)-3',4'-dihydronaphthalene](4a)

The mixture of nitro compounds (5.0 g, 0.019 mol) was dissolved in 70 ml of DMF and hydrogenated at 30 psi with 10% Pd on charcoal for 90 min. The filtered solution was evaporated to dryness and dissolved in a minimun amount of 1N HCl. Concentrated ammonium hydroxide was then added to the solution and the precipitated product washed with water and dried to give 3.2 g (72%) of the momoamines, mp 300° C. A mixture of amines (5 g), ethylene oxide (15 ml), acetic acid (25 ml) and water (25 ml) was stirred at ambient temperature (about 22° C.-27° C.) for 17 h. The solid obtained after evaporation on TLC analysis (silica gel, 10% isopropanol in ethyl acetate) showed two close spots, ca. R$_f$=0.4, corresponding to the two isomers. The solid was recyrstallized three times from water giving 0.250 g (3.6%0 of pure 5a, mp 187°-190° C.; NMR (Me$_2$SO-d$_6$)δ 1.77 (m, 2H, CH$_2$-3'), 2.68 (m, 4H, CH$_2$-1' and CH$_2$-4'), 3.00 (m, 4H, NCH$_2$CH$_2$OH), 3.40 (m, 4H, NCH$_2$CH$_2$OH), 4.38 (t, 2H, J=5.3 Hz, OH, D$_2$O exchanged), 6.77 (dd, 1H, J=6.3 Hz, J'-2.0 Hz, H-6'), 7.04 (m, 2H, H-7' and H-8'), 8.36 (s, 1H, N$_3$-H), 10.66 (s, 1H, N$_1$-H). Anal. (C$_{16}$H$_{21}$N$_3$O$_4$) C, H, N.

The remaining aqueous solution was evaporated, triturated with methanol and the residual solid recrystallized twice from water to give 0.3 g (4.3%) of pure 4a, mp 190°-192° C., NMR (Me$_2$SO-d$_6$)δ 1.79 (m, 2H, CH$_2$-3'), 2.70-3.20 (m, 4H, CH$_2$-1' and CH$_2$-4'), 3.31 (m, 4H, NCH$_2$CH$_2$OH), 3.45 (m, 4H, NCH$_2$CH$_2$OH), 4.67 (br t, 2H, OH, D$_2$O exchanged), 6.33 (d, 1H, J=2.0 Hz, H-8'), 6.47 (dd, 1H, J=8.4 Hz, J'=2.0 Hz, H-6'), 6.86 (d, 1H, J=8.4 Hz, H-5'), 8.23 (s, 1H, N$_3$-H), 10.63 (s, 1H, N$_1$-H). Anal. (C$_{16}$H$_{21}$N$_3$O$_4$) C, H, N.

DL-5'[Bis(2-chloroethyl)amino]spiro[2,5-imidazolidinedione-4,2'(1'H)-3',4'-dihydronaphthalene](5b)

Compound 5a (1.0 g, 0.0031 mol) was stirred overnight with freshly distilled POCl$_3$ (10 ml, 0.1 mol) at room temperature. The reaction mixture was evaporated to a syrup and then coevaporated with benzene. The residue obtained was dissolved in concentrated HCl and evaporated again. The remaining semisolid was purified by silica gel chromatography with ethyl acetate to give 0.38 g (34%) of 5b as a white solid, mp 180°-184° C.; NMR (Me$_2$SO-d$_6$)δ 1.79 (m, 2H, CH$_2$-3'), 2.70-3.30 (m, 4H, CH$_2$-1' and CH$_2$4'), 3.32 (m, 4H, NCH$_2$CH$_2$Cl), 3.53 (m, 4H, NCH$_2$CH$_2$Cl 6.88 (dd, 1H, J=3.1 Hz, J'=1.4 Hz, H-6'), 7.10 (m, 2H, H-7' and H-8'), 8.39 (s, 1H, N$_3$-H), 10.69 9s, 1H, N-H).

Anal. (C$_{16}$H$_{19}$N$_3$Cl$_2$O$_2$), C, H, N, Cl.

This compound was also isolated from a reaction starting with a mixture of both bis(2-hydroxyethyl)amino compound. After workup, column chromatography over silica gel with ethyl acetate-hexane (1:1) produced a faster moving isomer which corresponded exactly to this material.

DL-7'-[Bis(2-chloroethyl)amino]spiro[2,5-imidazolidine-4,2'(1'H)-3',4'-dihydronaphthalene](4b)

In reaction similar to that described above, compound 4a was converted to 4b which was isolated as a white solid, mp 212° C., NMR (Me$_2$SO-d$_6$) δ 1.70 (m, 2H, CH$_2$-3'), 2.70-3.30 (m, 4H, Ch$_2$-1' and Ch$_2$4'), 3.35-3.60 (m, 8H, NCH$_2$CH$_2$Cl), 6.43 (d, 1H, J=2.0 Hz, H-8'), 6.56 (dd, 1H, J=8.6 Hz, J'=2.0 Hz, H-6'), 6.93 (d, 1H, J=8.6 Hz, H-5'), 8.25 (s, 1H, $N_3$-H), 10.64 (s, 1H, $N_1$-H). Anal. ($C_{16}H_{19}N_3Cl_2O_2$) C, H, N, Cl.

This compound was also isolated from a reaction starting with a mixture of both bis(2-hydroxyethyl-)amino compounds. After workup, column chromatography over silica gel with ethyl acetate-hexane (1:1) produced a slower moving isomer which corresponded exactly to this material.

DL-2-Amino-7-bis(2chloroethyl)amino-1,2,3,4-tetrahydro-2-naphtholic acid. Hydrochloride salt (6)

The hydantoin mustard 4b (0.15 g) was dissolved in concentrated HCl and heated at 140° C. for 16 h in a sealed tube. The reaction mixture was evaporated in the cold (about 4° C. or less) and the residue dissolved in a small volume of 1N HCl and extracted with ethyl acetate several times. The aqueous fraction was lyophilized to give 40 mg of the 7-isomer mustard 6 which was 87% pure by GC-MS when analysed as a persilylated derivative;; mass spectrum, m/z (relative intensity) 474 ($M^+$, 5.7), 459 (M-$CH_3$, 2.2), 431 (M-$CH_3$-$C_2H_4$, 2.9) 402 M-$Me_3$Si+H, 3.7), 385 (M-$Me_3$SiN$H_2$, 1.9), 357 (M-$Me_3$Si$O_2$C, 100).

DL-2-Amino-5-bis-(2-chloroethyl)amino-1,2,3,4-tetrahydro-2-naphthoic acid. Hydrochloride salt (7).

Following similar procedure, the 5-isomer mustard 7 was isolated as a lyophilized powder which was 92% pure by GC-MS when analysed as a persilylated derivative; mass spectrum, m/z (relative intensity) 474 ($M^+$, 1.0), 459 (M-$CH_3$, 2.3), 431 (M-$CH_3$-$C_2H_4$, 2.4), 402 (M-$Me_3$Si+H, 1.7), 357 (M-$Me_3$Si$O_2$C, 100).

Transport Studies.

Murine L1210 Leukemia cells were grown in RPMI 1630 medium containing 16% heat-inactivated fetal calf serum and passaged over 2-3 days when cell densities approached $1 \times 10^6$ cells/ml. For experimental studies, cells were harvested from growth medium and washed twice in transport medium composed of, $CaCl_2.2H_2O$ (0.7 mM), $MgCl_2.6H_2O$) 0.5 mM, choline chloride (125 mM), HEPES (25 mM), and salt-free bovine serum albumin (0.1 mM). The final pH of the transport medium was 7.4. Cells were then incubated with 1.5 μM or 3.0 μM 2-amino-bicyclo [2.2.1]heptane-2-carboxylic acid [carboxyl-$^{14}$C] (BCH) along with the indicated concentration of either L-phenylalanine mustard or DL-2-Amino-7-bis(2chloroethyl) amino-1,2,3,4-tetrahydro-2-naphthoic acid (6). The initial rate of transport of BCH was terminated at 40 sec by centrifugation of $1 \times 10^6$ cells through Versilube F-50 silicone oil. The cell pellets were solubilized in 0.2N NaOH, acidified and counted in a Packard 460 C liquid scintillation counter.

Evaluation of Antitumor and Myelosuppressive Activity

Murine L1210 leukemia cells were grown as described above under transport studies. Cells were harvested and washed twice in a fresh growth medium. Bone marrow cells were removed from femurs of male CDF$_1$ mice and washed twice in RPMI 1630 containing 16% heat-inactivated fetal calf serum. A cell suspension containing both 100 tumor cells/Ml and 100 CFU-C/ml ($1.0 \times 10^5$ nucleated cells/ml) was prepared and the cells co-exposed for 45 min to the respective drug in RPMI 1630 containing 16% heat-inactivated fetal calf serum. The cells were then harvested, washed twice in Mc-Coy's 5A medium supplemented with 10% fetal bovine serum, 20 units/ml penicillin and 20 μg/ml streptomycin. Cell survival was assessed following 1 week of growth in the same medium at 37° in a humidified atmosphere of 5% $CO_2$. Experimental points represent the mean of three separate platings. Pregnant mouse uterine extract was used as a source of colony-stimulating factor for the bone marrow. The presence of either cell type had no effect on the plating efficiency of the other.

Determination of Alkylating Potency and Half Life ($t_{\frac{1}{2}}$).

The reaction of L-phenylalanine mustard and DL-2-Amino-7-bis(2-chloroethyl)amino-1,2,3,4-tetrahydro-2-naphthoic acid (6) with γ-(4-nitrobenzyl)pyridine was used to determine both alkylating potency and stability of the drugs in aqueous solution containing physiological concentrations of the chloride ion (Dulbecco's phosphate buffered saline). The drugs were made up as 65 mM stock solutions in 75% ethyl alcohol containing equimolar hydrochloric acid and diluted 200 fold into Dulbecco's phosphate buffered saline to initiate the study. One ml aliquots were removed at time=0, 7.5, 15, 60 and 135 min, the pH adjusted to 4.8 with 0.1M sodium acetate and residual alkylating activity determined as described by Truhaut et al. *Clin. Chim. Acta,* 1963, 8: 235, following reaction with γ-(4-nitrobenzyl)-pyridine. Experimental points represent the mean of three separate determinations.

Of course, the general procedures for the preparation of the hydantoin and amino acid nitrogen mustards are well known and found in such publication as Mauger and Ross, supra. However, at an early stage of the synthesis, Mauger and Ross were unable to separate and identify the mixture of the two mononitro derivatives obtained from β-tetralone hydantoin. Despite their success in the separation of one of the isomers at the bis-(2-hydroxy-ethyl)amino stage and its conversion to the final target amino acid mustard, the assigned location of the substituent for this isomer was still uncertain. Based on the comparative rates of hydrolysis of the final product with a group of standard tetrahydronaphthalene nitrogen mustards, the bis)2-chloroethyl)amino side chain was postulated to be a either the 5- or 8-position (Mauger and Ross, supra). It is noted that even the successful separation of the isomers at the nitro stage and their chemical oxidation to a nitrophthalic acid product, as suggested by these authors, could not have solved the issue of the substituent position.

The applicants resolved this issue by separating small amounts (ca. 200 mg) of both nitro-substituted isomers (see scheme 1) which were then analyzed by proton and carbon NMR spectoscopy to determine the exact position of the nitro group in the molecule (vide infra). It was easier, nevertheless, to continue the synthesis and perform the separation of isomers at the bis(2-hydroxyethyl)amino stage as described by Mauger and Ross, or even at the bis(2-chloroethyl)amino stage, prior to the hydrolysis of the hydantoin ring, as described more fully herein.

SCHEME 1

<sup>a</sup>HNO₃,
<sup>b</sup>H₂/Pd/C,
<sup>c</sup> ethylene oxide/HOAc,
<sup>d</sup>POCl₃,
<sup>e</sup>HCl The less water soluble bis(2-hydroxyethyl)amino isomer, mp 187°–190° C. (which corresponded to the material isolated by Mauger and Ross having a mp of 185°–187° C.), had to be either the 5- or the 8-substituted isomer based on its H-NMR spectrum that showed a pattern consistent with a 1,2,3-trisubstituted benzene (Table 1, compound 5a). This agreed well with the two alternative substitution sites suggested by the same authors which was based, as mentioned before, on the rate of hydrolysis of the final nitrogen mustard product (Mauger and Ross, supra). However, since the $^{13}$C-NMR spectral studies performed on the precursor nitro-substituted isomers 2 and 3 demonstrated that these compounds carried the nitro substituent exclusively and the 5- or the 7-position, the correct structure for the less water soluble bis(2-hydroxyethyl)amino isomer had to be 5a and the products derived from it has to correspond to the 5-substituted derivatives. The more water soluble bis-(2-hydroxyethyl)amino isomer, which was isolated from the mother solution (mp 190°–192° C.), had a $^1$H NMR spectrum consistent with a 1,2,4-trisubstituted benzene derivative (Table 1, compound 4a) and therefore had to correspond to the 7-substituted isomer.

TABLE 1

H—NMR Resonances of Aromatic Protons in Compounds 4 and 5.

[Structure: tetrahydronaphthalene with HO-CH2-CH2-N-CH2-CH2-OH group at position 6/7, numbered positions 1,2,3,4,4a,5,6,7,8,8a; side chain at position 2 with NH-C(=O) and N-H with O]

| Compound | H-5 | H-6 | H-7 | H-8 |
|---|---|---|---|---|
| 5a (5-isomer) | — | 6.77 dd $J_{6,7} = 6.3$ $J_{6,8} = 2.0$ | 7.04 m | 7.04 m |
| 4a (7-isomer) | 6.86 d $J_{5,6} = 8.4$ | 6.47 dd $J_{6,5} = 8.4$ $J_{6,8} = 2.0$ | — | 6.33 d $J_{8,6} = 2.0$ | s = singlet, d = doublet, dd = doublet of doublets, m = multiplet. Chemical shifts are in parts per million and J valves in Hertz. Al spectra were measured at 200 MHz in Me SO-d.

The remaining steps were performed essentially in the same manner as described by Mauger and Ross, supra; for both of the isomers 5- and 7-bis(2-hydroxyethyl)amino compounds to give the two rather unstable amino acid mustards 6 and 7 (Scheme 1). These compounds were readily hydrolyzed in aqueous solution to one arm mustards as confirmed by GC-MS (gas chromatographic and mass spectral) studies. For this reason the final products were not manipulated or purified any further and they were biologically evaluated as such. According to GC-MS studies, the purity for both isomers was about 90%. Reversed phase HPLC for the bologically important 7-isomer revealed a somewhat lower purity (about 74%) possible due to partial hydrolysis in the aqueous phase of the system (30 min gradient from water to 0.5M KH2PO4). All the other intermediates prior to the final amino acid mustards 6 and 7 were analytically pure as shown by spectral and combustion analysis.

Carbon NMR Spectral Studies

Absolute assignment of the site of nitration was accomplished by selective proton decoupling of the $^{13}C$-NMR. The faster moving isomer of the two nitro compounds collected after preparative HPLC showed a distinct 1,2,3 aromatic substitution pattern in its proton NMR spectrum indicating either 5- or 8-nitration. The fully coupled $^{13}C$-NMR showed the nonprotonated aromatic carbons at 148.9, 136.0 and 129.6 ppm (vide infra). The nitrated carbon resonance position (148.9) could be assigned based on its coupling pattern (doublet of doublets) since in either the 5- or the 8-nirto isomer, this carbon would show a $^2J$ (absolute value ~3 Hz)[17] and a $^3J$ (~9 Hz)[17] coupling to the neighboring aromatic protons (FIG. 1a). At this point, assignment of the other two nonprotonated carbon resonances (C-4a and C-8a) could be achieved by determining which showed coupling to the methylene protons at C-3 and was therefore C-4a. Coupling of C-8a to these methylene protons ($^4J$) would be very small and therefore undetectable at the available resolution. Selective decoupling of the H-1 and H-4 protons by irradiation of the overlapping resonances with decoupling power of 0.01 Watt simplified the resonances at 136.0 to a sharp doublet and the resonances at 129.6 to a broad triplet (FIG. 1b). Irradiation at a position midway between the overlapping H-1 and H-4 resonances and the H-3 resonance with a decoupling power of 0.02 Watt resulted in complete decoupling of the aliphatic protons and further simplified the resonance at 129.6 ppm to a sharper tiplet (FIG. 1C). The resonance at 129.6 ppm is therefore coupled to the H-3 protons and is C-4a. That C-4a is a triplet with a residual coupling constant of the magnitude of an aromatic $^3J$ (~5.2 Hz)[17] indicates that it is coupled through three bonds to two aromatic protons. These aromatic protons must be a H-6 and H-8 and the nitro group must therefore be at the 5 position (compound 3). The C-8a resonance at 136.0 is simplified to a doublet due to the residual coupling with H-7 ($^3J$); coupling with H-8 ($^2J$) is expected to be small (~1 Hz)[17] and is not resolved. X-ray crystallographic analysis performed on 5a confirmed the position of the side chain at C-5 in accordance with the NMR tests.

Similar strategy allowed the structural assignment of the second compound as the 7-nitro isomer (compound 2). In the aliphatic proton decoupled spectrum (FIG. 2c) the nitrated carbon (C-7) at 145.5 ppm appears as a doublet of triplets due to coupling through two bonds to H-6 and H-8 and through three bonds the H-5. C-4a, at 143.5 ppm, identified by its coupling to methlene protons at C-3, is coupled to two aromatic protons (h-6 and H-8 through three bonds and appears as a triplet. C-8a (134.6 ppm) is coupled to only one aromatic proton (H-5) through three bonds and is therefore a doublet.

Biological Tests

Figure 3A:
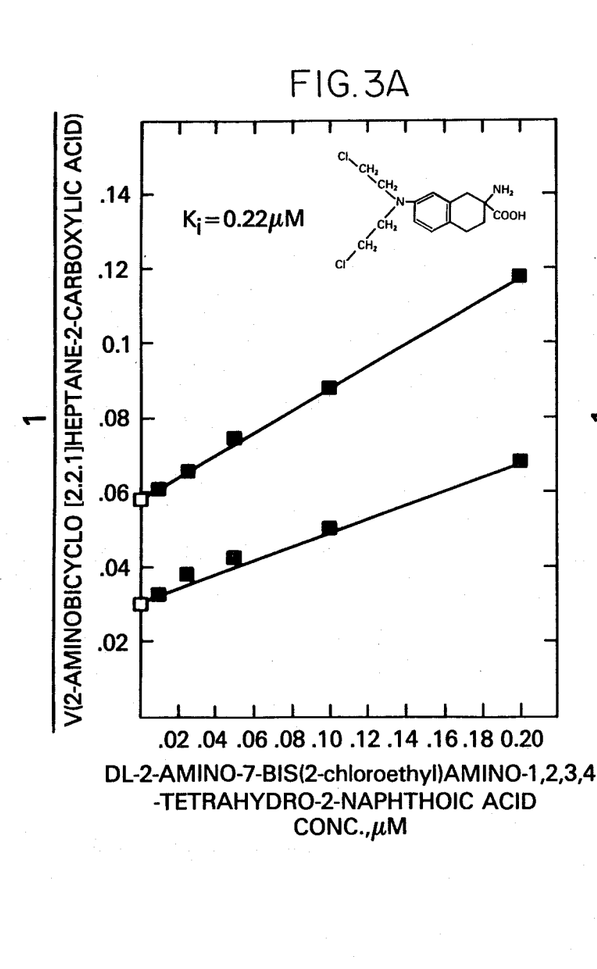
Figure 3B:
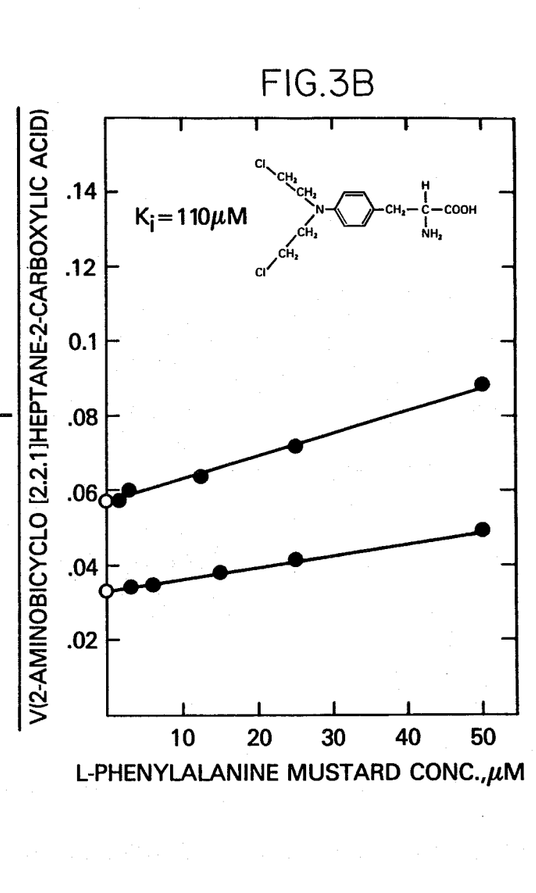

Compound 6 is an extremely potent competitive inhibitor of System L in murine L1210 leukemia cells (FIG. 3). Inhibition analysis of the initial rate of transport of BCH indicated that the $K_I$ is approximately 0.2 $\mu M$, 500-fold lower than that of L-phenylalanine mustard ($K_i = 100$ $\mu M$). This value indicates that the compound is a 25 to 50-fold more effective inhibitor of System L than BCH and approximately 40-fold more potent that 2-amino-1,2,3,4-tetrahydro-2-naphthoic acid (Vistica, et al., "Rational Basis for Chemotherapy", New York, 1983; p. 475). Compound 7, on the other hand, was a weaker inhibitor of System L with a $K_I$ of 15.2 $\mu M$ (data not shown).

Figure 4:
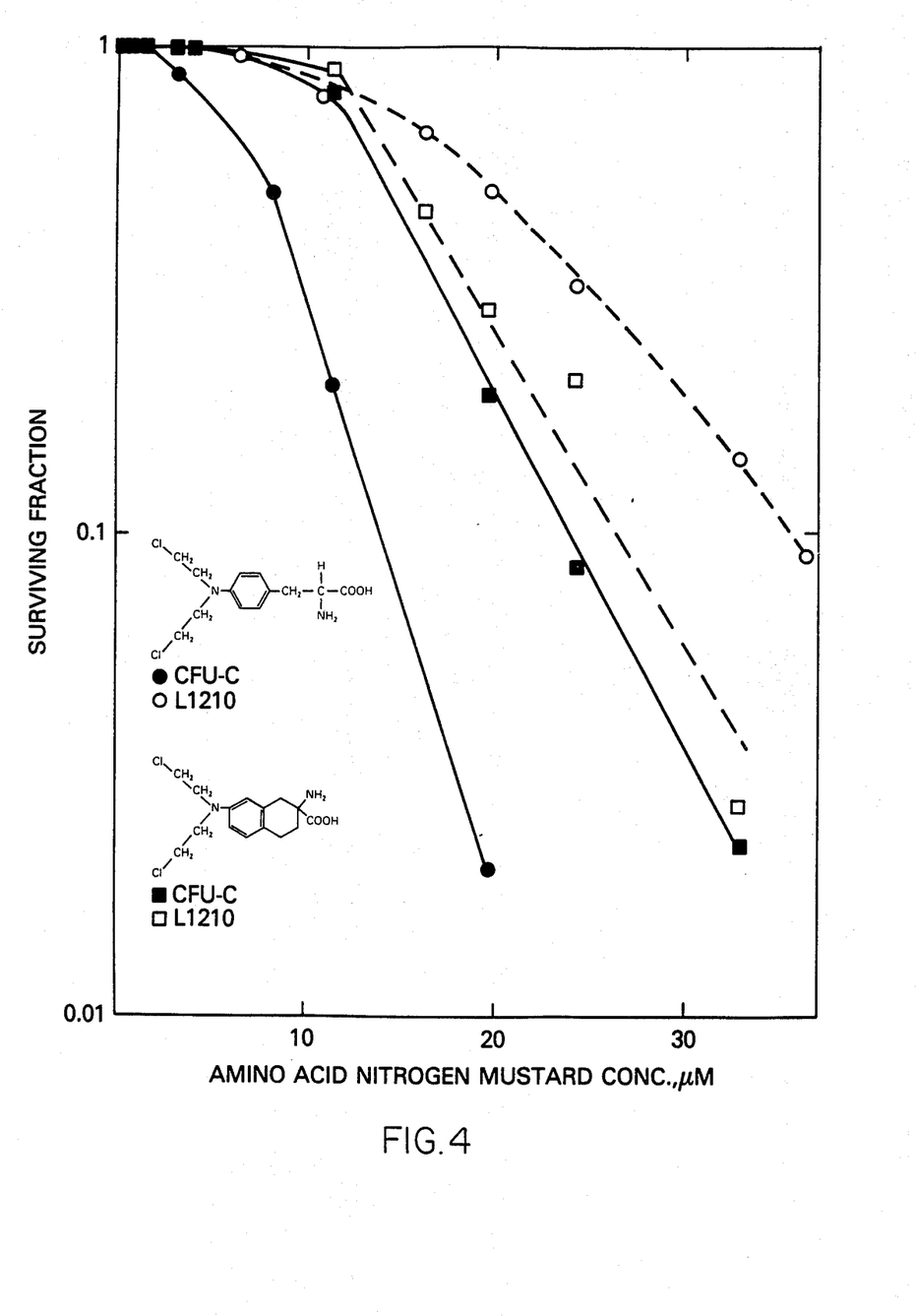
FIG. 4 shows the antitumor and myelosuppressive activity of L-PAM and compound 6.

L-Phenylalanine mustard, the prototype amino acid nitrogen mustard, is 2.5 times more cytotoxic to bone marrow progenitor cells than to murine L1210 leukemia cells (FIG. 4). The $LD_{90}$ concentration of L-PAM for murine CFU-C was 14 $\mu M$ as compared to 35 $\mu M$ for murine L1210 leukemia cells. Compound 6, on the other hand, possesses both enhanced antitumor activity ($LD_{90} = 26.5$ $\mu M$) and reduced myelosuppressive activity ($LD_{90} = 23.8$ $\mu M$) (FIG. 4). A comparison of the therapeutic indices for L-PAM and Compound 6 indicated a 2-2.5-fold improvement for the latter amino acid nitrogen mustard.

Figure 5:
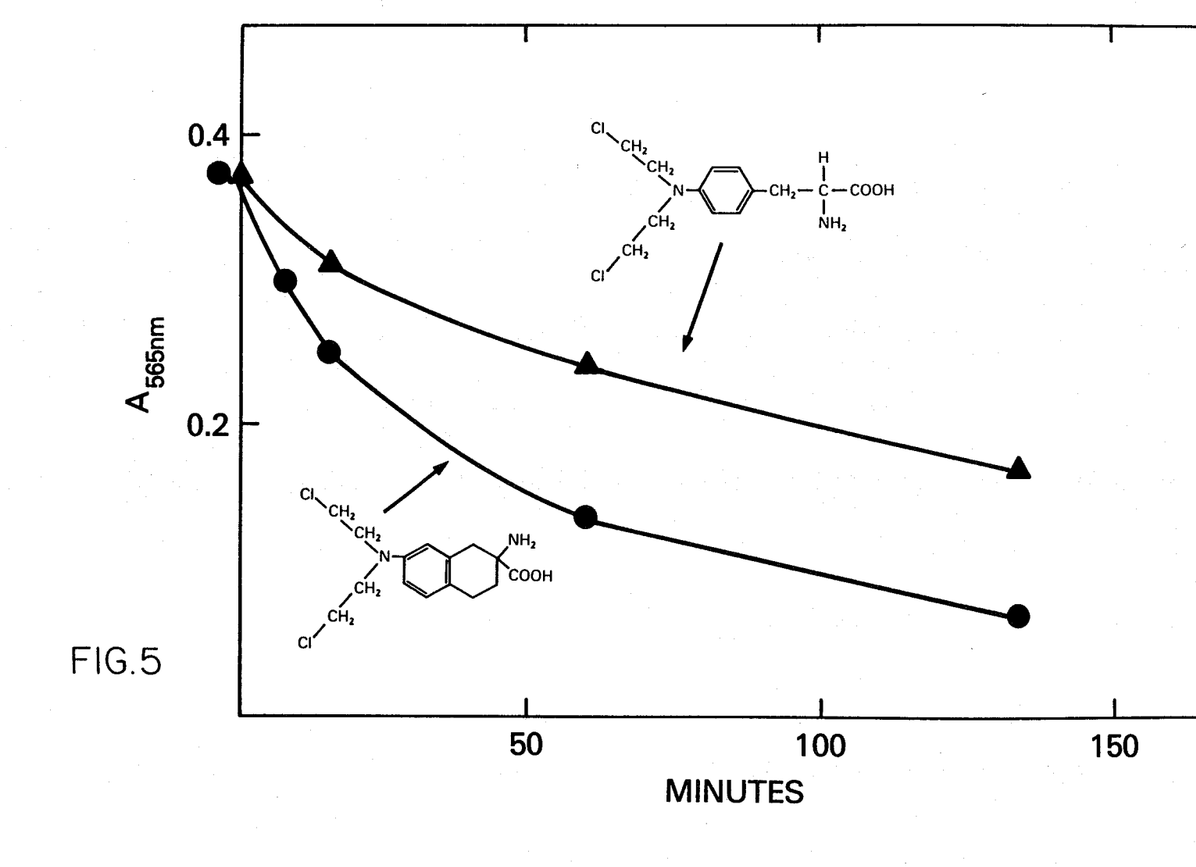
FIG. 5 shows the comparative rate of dechlorination of L-PAM and Compound 6.

Compound 6 and L-PAM possess identical alkylating capacity as determined by their reaction with $\gamma$-(4-nitrobenzyl)pyridine (FIG. 5). However these two amino acid nitrogen mustards differ significantly in their rate of dechlorination. Compound 6 has a half life ($t_{\frac{1}{2}}$) of approximately 40 minutes as compared to a 120 minutes for L-PAM.

The results presented here indicated that Compound 6 is the most potent inhibitor of System L, the sodium-independent leucine-preferring amino acid transport system. It is 25-50 times more effective than BCH and has a 500-fold greater affinity for System L than L-PAM. In addition to differing from L-PAM in its affinity for System L, compound 6 exhibits both enhanced antitumor and reduced myelosuppressive acitivity which results in a 2-fold improvement in the therapeutic index. Furthermore, the rate of dechlorination of compound 6 differs significantly from L-PAM, resulting in a 2-3-fold decrease in the $t_{\frac{1}{2}}$. Without being bound to any theory, it is hypthesized that this more rapid conversion to a non-cytotoxic derivative may be the reason for the observed increase in selectivity of compound 6. This could occur if the time required to achieve steady state concentrations of the drug in tumor cells is sufficiently short compared to its $t_{\frac{1}{2}}$. Residual drug would then be more rapidly dechlorinated resulting in a reduction of host toxicity. However, it is believed that the increase in selectivity may be primarily due to the avidity of compound 6 for System L. The high-affinity of the drug for that carrier system would result in higher intracellular concentrations of the drug in tumor cells; conversely, with an altered or absent System L in progenitor cells, lower concentrations would be expected in this sensitive host tissue, the result being a reduction in myelosuppression.

The compound of the present invention, such as DL-2-amino-7-bis(2-chloroethyl)amino-1,2,3,4-tetrahydro-2-naphthoic acid, of course has several utilities. First, the data with respect to murine tumor cells and murine bone marrow cells indicate that this drug is a potent antineoplastic agent which also exhibits improved selectivity against tumor cells. Specifically, it is less toxic to the bone marrow, the result being a reduction in myelosuppression at the therapeutic doses.

Secondly, since the drug exhibits the highest affinity of any compound ever described for the amino acid transport System L, it is useful in the treatment of brain tumors. System L is the only transport carrier which exists on the luminal side of the blood brain barrier. Administration of this drug, for example, intravenously, would allow the penetration of the drug through the blood brain barrier into the brain where the drug's antineoplastic properties would be effective against brain tumors.

Furthermore, by virtue of its high-affinity for the System L carrier, the drug can be used as a probe to isolate a cellular component amongst a heterogeneous mixture of other cellular macromolecules. This is accomplished as follows.

Cells are harvested from growth medium, centrifuged for 6 minutes at 300×g and then suspended in Dulbecco's phosphate buffered saline (PBS), pH 7.4, at $10^8$ cells/ml. The cells are disrupted by sonication and the sonicate treated with DNAse and RNase. The sonicate is then applied to a Sephadex G-25 column and the column eluted with PBS. The column void volume is collected and treated with 100 μM of DL-2-amino-7-bis(2-chloroethyl)amino-1,2,3,4-tetrahydro-2-naphthoic acid with or without 1 mM 2-aminobicyclo [2.2.1]heptane-2-carboxylic acid. The sonicate is applied to a Sephadex G-25 column and eluted with PBS. The latter procedure removes both unreacted and dechlorinated drug. The Sephadex G-25 eluant (void volume) is applied to a Sephraose 2B column and eluted with PBS with or without 1 mM 2-aminobicyclo [2.2.1]heptane-2-carboxylic acid. Fractions are collected and monitored at $A_{220}$ nM on a standard spectrophotometer. That fraction which exhibit absorbance at 220 nM and which is sensitive to (that is, inhibited by) 2-aminobicyclo [2.2.1]heptane-2-carboxylic acid is indicative of the presence of L-amino acid transport system and such fractions may be pooled for further study, if necessary.

Of course, the compounds of the present invention can also be labelled, for example with radioisotopes and such raiolabelled compounds employed cytochemically or otherwise, for identification of the system L-carrier.

Of course the pharmaceutical composition comprising the new antineoplastic compound(s) of the present invention as an active ingredient in an amount sufficient to produce antineoplastic effect in a susceptible host or tissue and a pharmaceutically acceptable carrier, can also be easily prepared from the disclosure contained herein. Such pharmaceutical compositions may be in any suitable form such as a liquid, solid or semi solid, for example an injectable solution, tablet, capsule, ointment, lotion and the like. It could be applied either topically or systemically or both.

It is understood that the examples and embodiments described herein are for illustrative purposed only and that various modifications or changes in light thereof will be suggested to persons skilled in the art and are to be included within the spirit and purview of this application and scope of the appended claims.

What is claimed is:

1. DL-2-amino-7-bis(2-chloroethyl)amino-1,2,3,4-tetrahydro-2-naphthoic acid.

2. A pharmaceutical composition comprising DL-2-amino-7-bis(2-chloroethyl)amino-1,2,3,4-tetrahydro-2-naphthoic acid as an active ingredient in an amount sufficient to produce antineoplastic effect in a susceptible host or tissue and a pharmaceutically acceptable carrier.

* * * * *